US012653402B2

(12) United States Patent (10) Patent No.: US 12,653,402 B2

Franke et al. (45) Date of Patent: Jun. 16, 2026

(54) INTRAORAL CAMERA

(71) Applicant: DENTSPLY SIRONA Inc., York, PA (US)

(72) Inventors: Frederike Franke, Darmstadt (DE); Bjoern Voss, Bensheim (DE); Thomas Ertl, Usingen (DE); Michael Tewes, Bruhl (DE); Andreas Unger, Gross-Gerau (DE)

(73) Assignee: Dentsply Sirona Inc., York, PA (US)

( * ) Notice: Subject to any disclaimer, the term of this patent is extended or adjusted under 35 U.S.C. 154(b) by 302 days.

(21) Appl. No.: 18/493,174

(22) Filed: Oct. 24, 2023

(65) Prior Publication Data

US 2025/0127401 A1 Apr. 24, 2025

(51) Int. Cl.
A61B 5/00 (2006.01)
A61B 1/24 (2006.01)

(52) U.S. Cl.
CPC .............. A61B 5/0088 (2013.01); A61B 1/24 (2013.01); A61B 5/0073 (2013.01); A61B 5/4547 (2013.01); *A61B 5/0035* (2013.01)

(58) Field of Classification Search
CPC ....... A61B 5/0088; A61B 1/24; A61B 5/0073; A61B 5/4547
See application file for complete search history.

(56) References Cited

U.S. PATENT DOCUMENTS

| | | | | |
|---|---|---|---|---|
| 11,049,606 B2 * | 6/2021 | Johnson | ................. | G16H 50/20 |
| 11,189,028 B1 * | 11/2021 | Kearney | .............. | A61B 6/5217 |

| | | | | |
|---|---|---|---|---|
| 11,217,350 B2 * | 1/2022 | Kearney | ................ | G16H 70/60 |
| 11,238,374 B2 * | 2/2022 | Kao | ........................ | G06N 20/00 |
| 11,238,576 B2 * | 2/2022 | Miki | ........................ | G06N 3/08 |
| 11,276,151 B2 * | 3/2022 | Kearney | .............. | G06T 7/0014 |
| 11,288,602 B2 * | 3/2022 | Jones | ................... | G06N 20/20 |
| 11,311,247 B2 * | 4/2022 | Kearney | ................ | A61B 6/51 |
| 11,315,242 B2 * | 4/2022 | Katouzian | ............. | G06V 10/87 |
| 11,341,361 B2 * | 5/2022 | Kubota | ............... | G06V 10/771 |
| 11,348,237 B2 * | 5/2022 | Kearney | ................ | G16H 50/20 |
| 11,357,604 B2 * | 6/2022 | Kearney | .............. | G06N 3/088 |
| 11,366,985 B2 * | 6/2022 | Kearney | .............. | G06N 3/098 |
| 11,367,188 B2 * | 6/2022 | Kearney | .............. | G06N 3/098 |
| 11,389,131 B2 * | 7/2022 | Tuzoff | ...................... | G06T 7/11 |
| 11,398,013 B2 * | 7/2022 | Kearney | .................. | G06T 5/70 |
| 11,410,302 B2 * | 8/2022 | Huang | ................... | G06V 10/82 |

(Continued)

FOREIGN PATENT DOCUMENTS

EP 4544979 A1 4/2025

OTHER PUBLICATIONS

Daniel Fried, Detecting Dental Decay with Infrared Light, May 2020, Optics and Photonics News, pp. 50-53 (Year: 2020).*

(Continued)

*Primary Examiner* — Mohammed H Zuberi

(74) *Attorney, Agent, or Firm* — SCHWEGMAN LUNDBERG & WOESSNER, P.A.

(57) ABSTRACT

Light is projected from a light source in a first direction towards a tooth. The light source generates at least infrared light in the wavelength range of 950 nm to 2500 nm. A colloidal quantum dot (CQD) sensor records one or more surface light distribution images produced at the surface of the tooth by the projected light and the one or more surface light distribution images are used to compute a defect condition of the tooth.

17 Claims, 7 Drawing Sheets

PROVIDE AN INTRA-ORAL CAMERA COMPRISING A LIGHT SOURCE 702

PROJECT LIGHT FROM THE LIGHT SOURCE IN A FIRST DIRECTION TOWARDS AT LEAST ONE TOOTH, THE LIGHT SOURCE IS CONFIGURED TO GENERATE AT LEAST INFRARED LIGHT IN THE WAVELENGTH RANGE OF 950NM TO 1600NM 704

RECORD, BY A COLLOIDAL QUANTUM DOT (CQD) SENSOR, ONE OR MORE SURFACE LIGHT DISTRIBUTION IMAGES PRODUCED AT THE SURFACE OF THE AT LEAST ONE TOOTH BY THE PROJECTED LIGHT 706

COMPUTE, USING THE ONE OR MORE SURFACE LIGHT DISTRIBUTION IMAGES, A DEFECT CONDITION OF THE AT LEAST ONE TOOTH 708

(56) References Cited

U.S. PATENT DOCUMENTS

| | | | | |
|---|---|---|---|---|
| 11,423,538 B2 * | 8/2022 | Vianu | ................... | G06V 30/333 |
| 11,464,467 B2 * | 10/2022 | Ezhov | .................... | A61B 5/743 |
| 11,521,310 B2 * | 12/2022 | Lin | ......................... | G06V 10/74 |
| 11,889,991 B2 * | 2/2024 | Elazar | ................. | F21V 33/0068 |
| 2012/0320445 A1 * | 12/2012 | Yang | ....................... | G02B 5/201 |
| | | | | 359/290 |
| 2013/0278716 A1 * | 10/2013 | Kennedy | ................ | H04N 13/20 |
| | | | | 348/42 |
| 2014/0272764 A1 * | 9/2014 | Miller | .................... | A61B 1/051 |
| | | | | 433/29 |
| 2016/0113746 A1 * | 4/2016 | Bringley | .................. | A61K 6/62 |
| | | | | 433/29 |
| 2019/0313963 A1 * | 10/2019 | Hillen | ..................... | G06N 3/09 |
| 2022/0231244 A1 * | 7/2022 | Klem | .................... | H10K 30/88 |
| 2023/0025243 A1 * | 1/2023 | Atiya | ................... | A61B 5/0088 |
| 2023/0071509 A1 * | 3/2023 | Hinds | .................... | G01J 1/0411 |
| 2023/0168078 A1 * | 6/2023 | Klem | ..................... | G01B 11/22 |
| | | | | 356/51 |
| 2023/0222767 A1 * | 7/2023 | Ertl | ...................... | A61B 5/0071 |
| | | | | 600/408 |
| 2024/0339205 A1 * | 10/2024 | Lenzenhuber | ..... | G06K 7/10415 |

OTHER PUBLICATIONS

"European Application Serial No. 24208363.2, Extended European Search Report mailed Mar. 12, 2025", 10 pgs.

"European Application Serial No. 24208363.2, Response Filed Sep. 22, 2025 to Extended European Search Report mailed Mar. 12, 2025", 51 pgs.

Liu, Jing, "Flexible and broadband colloidal quantum dots photodiode array for pixel-level X-ray to near-infrared image fusion", Nature Communications, vol. 14, No. 1, (Sep. 2, 2023), 9 pgs.

Pejovic, Vladimir, "Infrared Colloidal Quantum Dot Image Sensors", IEEE Transactions on Electron Devices, IEEE, USA, vol. 69, No. 6, (Dec. 20, 2021), 2840-2850.

* cited by examiner

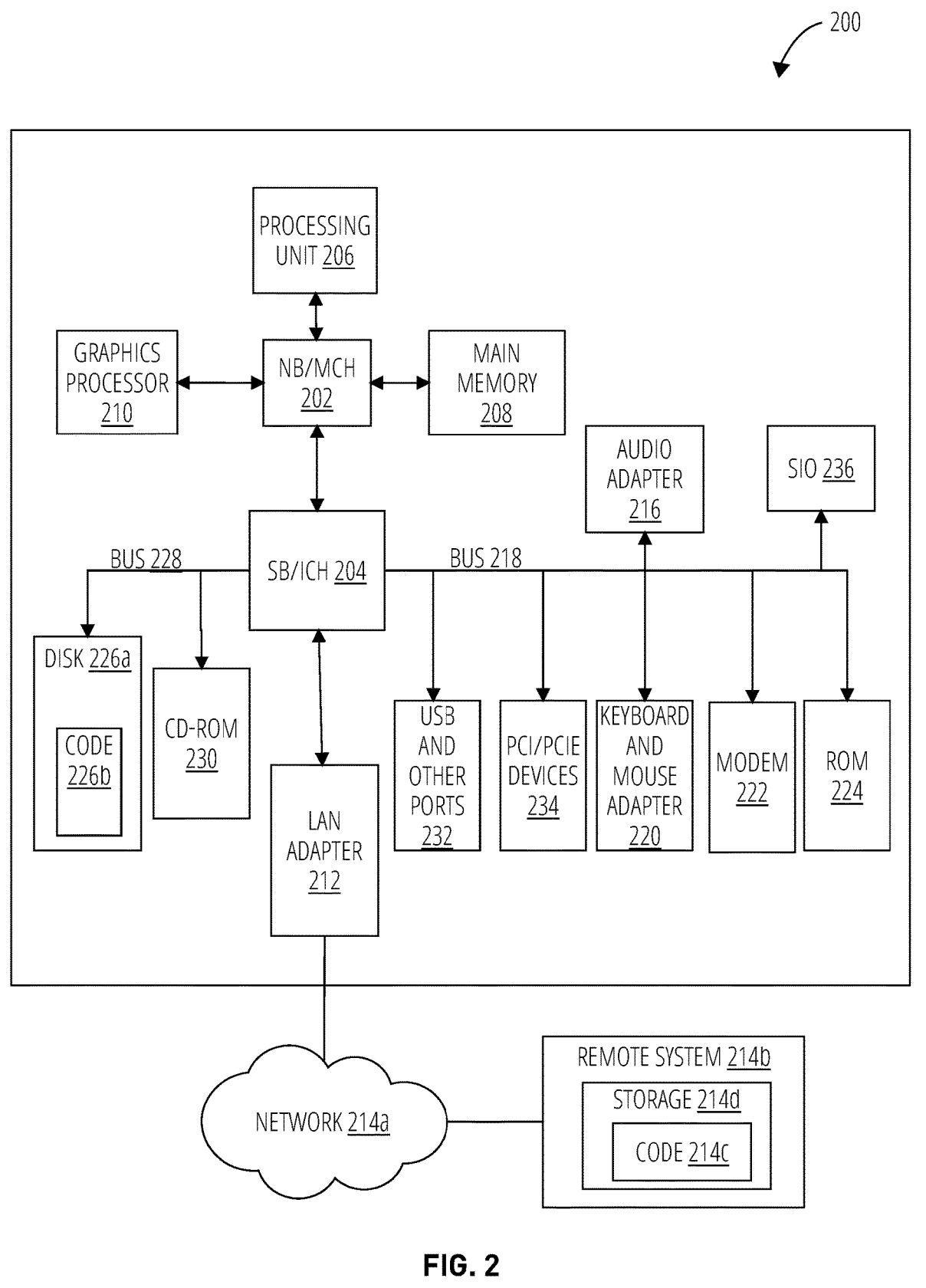

200

PROCESSING UNIT 206

GRAPHICS PROCESSOR 210

NB/MCH 202

MAIN MEMORY 208

AUDIO ADAPTER 216

SIO 236

BUS 228

SB/ICH 204

BUS 218

DISK 226a

CODE 226b

CD-ROM 230

LAN ADAPTER 212

USB AND OTHER PORTS 232

PCI/PCIE DEVICES 234

KEYBOARD AND MOUSE ADAPTER 220

MODEM 222

ROM 224

NETWORK 214a

REMOTE SYSTEM 214b

STORAGE 214d

CODE 214c

FIG. 2

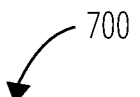

| PROVIDE AN INTRA-ORAL CAMERA COMPRISING A LIGHT SOURCE 702 |
|---|
| PROJECT LIGHT FROM THE LIGHT SOURCE IN A FIRST DIRECTION TOWARDS AT LEAST ONE TOOTH, THE LIGHT SOURCE IS CONFIGURED TO GENERATE AT LEAST INFRARED LIGHT IN THE WAVELENGTH RANGE OF 950NM TO 1600NM 704 |
| RECORD, BY A COLLOIDAL QUANTUM DOT (CQD) SENSOR, ONE OR MORE SURFACE LIGHT DISTRIBUTION IMAGES PRODUCED AT THE SURFACE OF THE AT LEAST ONE TOOTH BY THE PROJECTED LIGHT 706 |
| COMPUTE, USING THE ONE OR MORE SURFACE LIGHT DISTRIBUTION IMAGES, A DEFECT CONDITION OF THE AT LEAST ONE TOOTH 708 |

FIG. 7

INTRAORAL CAMERA

BACKGROUND

Technical Field

The present disclosure generally relates detecting defective tooth material and more particularly to an intraoral camera configured to detect defective tooth material based on long wavelength lights that produce limited light scattering in enamel.

Description of the Related Art

Intraoral cameras are handheld devices that can capture high-quality 2D and/or 3D images and videos of a patient's teeth and oral tissues. The intraoral cameras may include optics and built-in LED illumination for imaging, providing dentists with a valuable diagnostic tool, aiding in the detection of dental issues, and enhancing patient engagement and education.

BRIEF SUMMARY

According to an embodiment of the present disclosure, a method is disclosed. The method includes providing an intraoral camera including a light source, projecting light from the light source in a first direction towards at least one tooth, the light source is configured to generate at least infrared light in the wavelength range of 950 nm to 2500 nm, recording, by a colloidal quantum dot (CQD) sensor, one or more surface light distribution images produced at the surface of the at least one tooth by the projected light, and computing, using the one or more surface light distribution images, a defect condition of the at least one tooth.

In an aspect, the wavelength range is 1000 nm to 1300 or 950 to 1600 nm. In an aspect, the light source is configured to project visible light. In an aspect, the intraoral camera is further configured to measure three-dimensional (3D) information about the at least one tooth.

According to an embodiment of the present disclosure, an intraoral camera system is disclosed. The system includes a light source configured to generate at least infrared light in the wavelength range of 950 nm to 2500 nm. The intraoral camera system also includes a colloidal quantum dot (CQD) sensor. The intraoral camera system also includes a processor configured to project light from the light source in a first direction towards at least one tooth, record, by the CQD sensor, one or more surface light distribution images produced at the surface of the at least one tooth by the projected light, and, compute, using the one or more surface light distribution images, a defect condition of the at least one tooth.

According to an embodiment of the present disclosure, a non-transitory computer readable storage medium storing one or more programs is disclosed. The program when executed by a processor causes the intraoral camera to project light from a light source of an intraoral camera in a first direction towards at least one tooth, record, by a colloidal quantum dot (CQD) sensor, one or more surface light distribution images produced at the surface of the at least one tooth by the projected light, and compute, using the one or more surface light distribution images, a defect condition of the at least one tooth. The light source is configured to generate at least infrared light in the wavelength range of 950 nm to 2500 nm.

BRIEF DESCRIPTION OF THE DRAWINGS

To easily identify the discussion of any particular element or act, the most significant digit or digits in a reference number refer to the figure number in which that element is first introduced.

FIG. 2 depicts a block diagram of a data processing system in accordance with an illustrative embodiment.

FIG. 7 depicts a routine in accordance with an illustrative embodiment.

DETAILED DESCRIPTION

The illustrative embodiments recognize that caries and other structural defects are oftentimes beneath the tooth surface. As light of longer wavelength scatters less in enamel, it may be possible to image such features with infrared light. The longer the wavelength, the less light scatters in enamel and the more transparent it becomes.

The illustrative embodiments disclose projecting light from a light source in a first direction towards at least one tooth. The light source generates at least infrared light in the wavelength range of 950 nm to 2500 nm. A colloidal quantum dot (CQD) sensor may record one or more surface light distribution images produced at the surface of the at least one tooth by the projected light and the one or more surface light distribution images are used to compute a defect condition of the at least one tooth.

The illustrative embodiments are described with respect to certain types of data, functions, algorithms, equations, model configurations, locations of embodiments, additional data, devices, data processing systems, environments, components, and applications only as examples. Any specific manifestations of these and other similar artifacts are not intended to be limiting to the invention. Any suitable manifestation of these and other similar artifacts can be selected within the scope of the illustrative embodiments.

Figure 1:
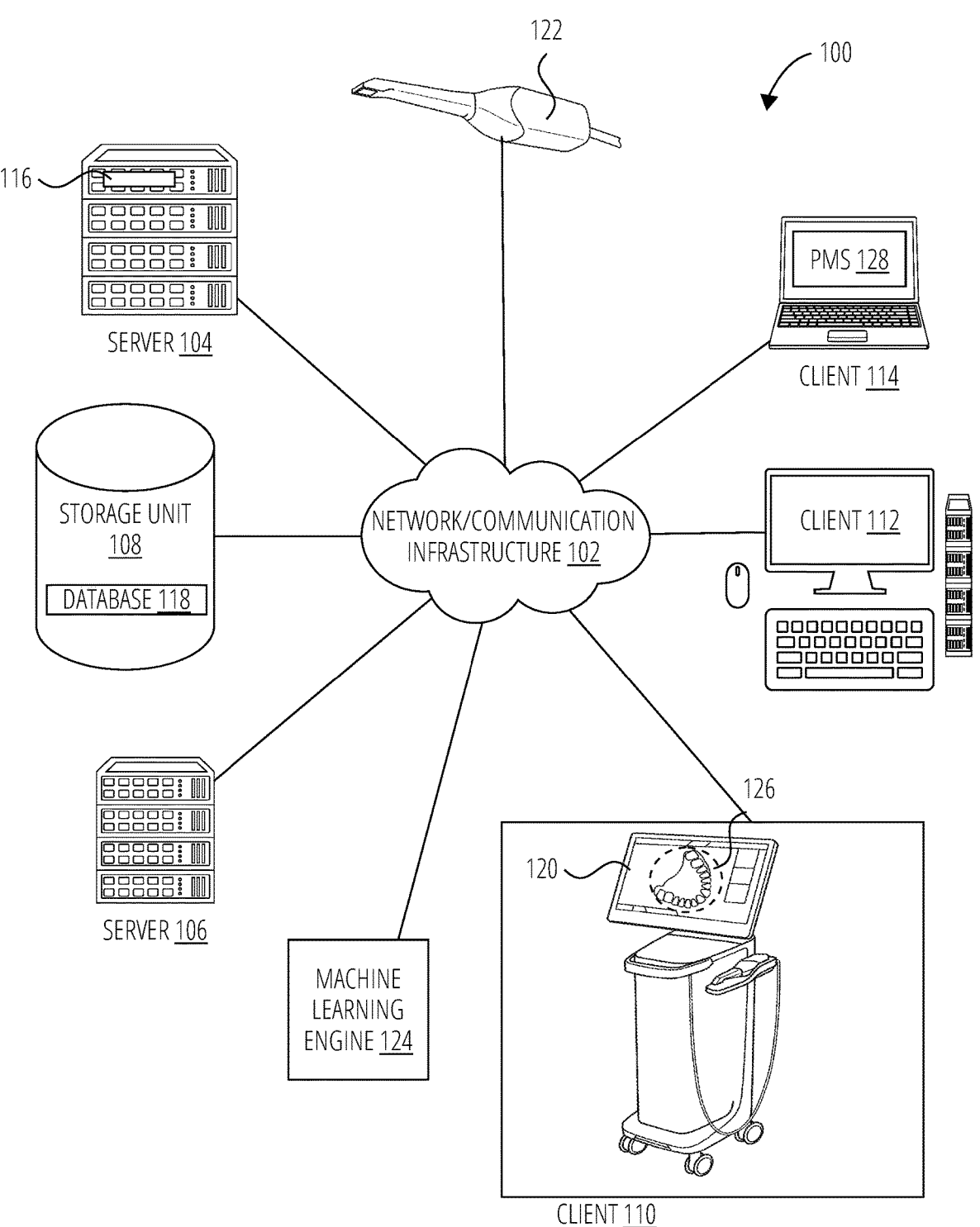
FIG. 1 depicts a block diagram of a network of data processing systems in accordance with an illustrative embodiment.

Any advantages listed herein are only examples and are not intended to be limiting to the illustrative embodiments. Additional or different advantages may be realized by specific illustrative embodiments. Furthermore, a particular illustrative embodiment may have some, all, or none of the advantages listed above. With reference to the figures and in particular with reference to FIG. 1 and FIG. 2, these figures are example diagrams of data processing environments in which illustrative embodiments may be implemented. FIG. 1 and FIG. 2 are only examples and are not intended to assert or imply any limitation with regard to the environments in which different embodiments may be implemented. A particular implementation may make many modifications to the depicted environments based on the following description.

FIG. 1 depicts a block diagram of an environment of data processing systems in which illustrative embodiments may be implemented. Data processing environment 100 is a network of computers in which the illustrative embodiments may be implemented. Data processing environment 100 includes network/communication infrastructure 102. Network/communication infrastructure 102 is the medium used to provide communications links between various devices, databases and computers connected together within data processing environment 100. Network/communication infrastructure 102 may include connections, such as wire, wireless communication links, or fiber optic cables.

Clients or servers are only example roles of certain data processing systems connected to network/communication infrastructure 102 and are not intended to exclude other configurations or roles for these data processing systems. Server 104 and server 106 couple to network/communication infrastructure 102 along with storage unit 108. Software applications may execute on any computer in data processing environment 100. Client 110, client 112, client 114 are also coupled to network/communication infrastructure 102. Client 110 may be a dental acquisition unit with a display. A data processing system, such as server 104 or server 106, or clients (client 110, client 112, client 114) may include data and may have software applications or software tools executing thereon. Client 114 or any other clients or data processing systems may include a practice management system 128 (PMS). The practice management system 128 may alternatively, or in addition be a standalone system use in a practice for managing patient data.

Only as an example, and without implying any limitation to such architecture, FIG. 1 depicts certain components that are usable in an example implementation of an embodiment. For example, servers and clients are only examples and do not to imply a limitation to a client-server architecture. As another example, an embodiment can be distributed across several data processing systems and a data network as shown, whereas another embodiment can be implemented on a single data processing system within the scope of the illustrative embodiments. Data processing systems (server 104, server 106, client 110, client 112, client 114) also represent example nodes in a cluster, partitions, and other configurations suitable for implementing an embodiment.

Intraoral camera 122 includes one or more sensors, such as colloidal quantum dot (CQD) sensors, CMOS sensors or others which are used to detect defects in tooth. In an example, the intraoral camera 122 captures data points to detect defects as well as to register the sizes and shapes of each tooth. The intraoral camera 122 continuously sends this data to the connected computer's software for computations or analysis.

Client application 120 or any other application such as server application 116 implements an embodiment described herein. Client application 120 and/or server application 116 can use data from intraoral camera 122 for tooth defect detection and for generating 3D jaw models and color images of one or more teeth 308. Client application 120 can also execute in any of data processing systems (server 104 or server 106, client 110, client 112, client 114), such as client server application 116 in server 104 and need not execute in the same system as client 110.

Machine learning engine 124 may compute a defect condition of the at least one tooth by classifying one or more surface light distribution images 126 based a change in light distribution in the one or more surface light distribution images caused by a defective tooth material. Machine learning engine 124 may be a part of, or separate from server 104 or clients 110, 112 and 114. The machine learning engine 124 may be trained based on a plurality of test surface light distribution images 126 that contain defective tooth material data.

Server 104, server 106, storage unit 108, client 110, client 112, client 114, may couple to network/communication infrastructure 102 using wired connections, wireless communication protocols, or other suitable data connectivity. Client 110, client 112 and client 114 may be, for example, personal computers or network computers.

In the depicted example, server 104 may provide data, such as boot files, operating system images, and applications to client 110, client 112, and client 114. Client 110, client 112 and client 114 may be clients to server 104 in this example. Client 110, client 112 and client 114 or some combination thereof, may include their own data, boot files, operating system images, and applications. Data processing environment 100 may include additional servers, clients, and other devices that are not shown. Server 104 includes the server application 116 that may be configured to implement one or more of the functions described herein for displaying restoration proposals in accordance with one or more embodiments.

Server 106 may include a search engine configured to search stored files such as images of patient teeth for comparison in response to a request for detecting tooth defects. In the depicted example, data processing environment 100 may be the Internet. Network/communication infrastructure 102 may represent a collection of networks and gateways that use the Transmission Control Protocol/Internet Protocol (TCP/IP) and other protocols to communicate with one another. At the heart of the Internet is a backbone of data communication links between major nodes or host computers, including thousands of dental practices, commercial, governmental, educational, and other computer systems that route data and messages. Of course, data processing environment 100 also may be implemented as a number of different types of networks, such as for example, an intranet, a local area network (LAN), or a wide area network (WAN). FIG. 1 is intended as an example, and not as an architectural limitation for the different illustrative embodiments.

Among other uses, data processing environment 100 may be used for implementing a client-server environment in which the illustrative embodiments may be implemented. A client-server environment enables software applications and data to be distributed across a network such that an application functions by using the interactivity between a client data processing system and a server data processing system. Data processing environment 100 may also employ a service-oriented architecture where interoperable software components distributed across a network may be packaged together as coherent business applications. Data processing environment 100 may also take the form of a cloud, and employ a cloud computing model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service.

With reference to FIG. 2, this figure depicts a block diagram of a data processing system in which illustrative embodiments may be implemented. Data processing system 200 is an example of a computer, such client 110, client 112, client 114 or server 104, server 106, in FIG. 1, or another type of device in which computer usable program code or instructions implementing the processes may be located for the illustrative embodiments.

Data processing system 200 is described as a computer only as an example, without being limited thereto. Implementations in the form of other devices, may modify data processing system 200, such as by adding a touch interface, and even eliminate certain depicted components from data processing system 200 without departing from the general description of the operations and functions of data process-ing system 200 described herein.

In the depicted example, data processing system 200 employs a hub architecture including North Bridge and memory controller hub (NB/MCH) 202 and South Bridge and input/output (I/O) controller hub (SB/ICH) 204. Pro-cessing unit 206, main memory 208, and graphics processor 210 are coupled to North Bridge and memory controller hub (NB/MCH) 202. Processing unit 206 may include one or more processors and may be implemented using one or more heterogeneous processor systems. Processing unit 206 may be a multi-core processor. Graphics processor 210 may be coupled to North Bridge and memory controller hub (NB/MCH) 202 through an accelerated graphics port (AGP) in certain implementations.

In the depicted example, local area network (LAN) adapter 212 is coupled to South Bridge and input/output (I/O) controller hub (SB/ICH) 204. Audio adapter 216, keyboard and mouse adapter 220, modem 222, read only memory (ROM) 224, universal serial bus (USB) and other ports 232, and PCI/PCIe devices 234 are coupled to South Bridge and input/output (I/O) controller hub (SB/ICH) 204 through bus 218. Hard disk drive (HDD) or solid-state drive (SSD) 226a and CD-ROM 230 are coupled to South Bridge and input/output (I/O) controller hub (SB/ICH) 204 through bus 228. PCI/PCIe devices 234 may include, for example, Ethernet adapters, add-in cards, and PC cards for notebook computers. PCI uses a card bus controller, while PCIe does not. Read only memory (ROM) 224 may be, for example, a flash binary input/output system (BIOS). Hard disk drive (HDD) or solid-state drive (SSD) 226a and CD-ROM 230 may use, for example, an integrated drive electronics (IDE), serial advanced technology attachment (SATA) interface, or variants such as external-SATA (eSATA) and micro-SATA (mSATA). A super I/O (SIO) device 236 may be coupled to South Bridge and input/output (I/O) controller hub (SB/ICH) 204 through bus 218.

Memories, such as main memory 208, read only memory (ROM) 224, or flash memory (not shown), are some examples of computer usable storage devices. Hard disk drive (HDD) or solid-state drive (SSD) 226a, CD-ROM 230, and other similarly usable devices are some examples of computer usable storage devices including a computer usable storage medium.

An operating system runs on processing unit 206. The operating system coordinates and provides control of vari-ous components within data processing system 200 in FIG. 2. The operating system may be a commercially available operating system for any type of computing platform, including but not limited to server systems, personal com-puters, and mobile devices. An object oriented or other type of programming system may operate in conjunction with the operating system and provide calls to the operating system from programs or applications executing on data processing system 200.

Instructions for the operating system, the object-oriented programming system, and applications or programs, such as server application 116 and client application 120 in FIG. 1, are located on storage devices, such as in the form of codes 226b on Hard disk drive (HDD) or solid-state drive (SSD) 226a, and may be loaded into at least one of one or more memories, such as main memory 208, for execution by processing unit 206. The processes of the illustrative embodiments may be performed by processing unit 206 using computer implemented instructions, which may be located in a memory, such as, for example, main memory 208, read only memory (ROM) 224, or in one or more peripheral devices.

Furthermore, in one case, code 226b may be downloaded over network 214a from remote system 214b, where similar code 214c is stored on a storage device 214d in another case, code 226b may be downloaded over network 214a to remote system 214b, where downloaded code 214c is stored on a storage device 214d.

A communications unit may include one or more devices used to transmit and receive data, such as a modem or a network adapter. A memory may be, for example, main memory 208 or a cache, such as the cache found in North Bridge and memory controller hub (NB/MCH) 202. A processing unit may include one or more processors or CPUs.

Where a computer or data processing system is described as a virtual machine, a virtual device, or a virtual compo-nent, the virtual machine, virtual device, or the virtual component operates in the manner of data processing system 200 using virtualized manifestation of some or all compo-nents depicted in data processing system 200. For example, in a virtual machine, virtual device, or virtual component, processing unit 206 is manifested as a virtualized instance of all or some number of hardware processing units 206 available in a host data processing system, main memory 208 is manifested as a virtualized instance of all or some portion of main memory 208 that may be available in the host data processing system, and Hard disk drive (HDD) or solid-state drive (SSD) 226a is manifested as a virtualized instance of all or some portion of Hard disk drive (HDD) or solid-state drive (SSD) 226a that may be available in the host data processing system. The host data processing sys-tem in such cases is represented by data processing system 200.

Figure 3:
FIG. 3 depicts a sketch of an intraoral camera system in accordance with an illustrative embodiment.
Figure 3:
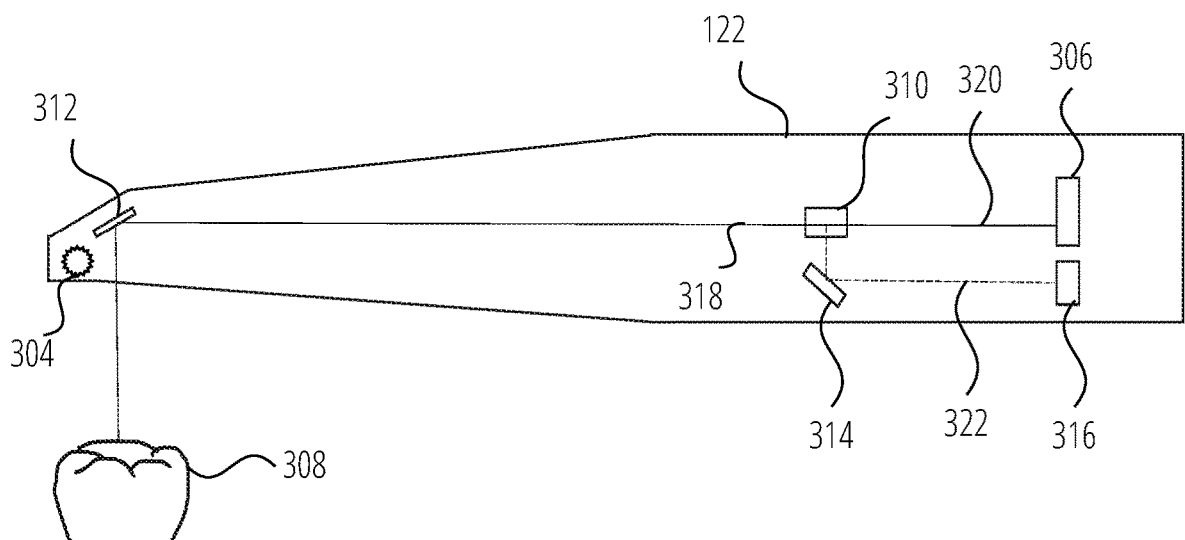

Turning now to FIG. 3, an intraoral camera system 302 is shown depicting an illustrative embodiment. The intraoral camera system 302 comprises an intraoral camera 122 that comprises a light source 304 configured to generate at least infrared light in the wavelength range of 950 nm to 2500 nm. In some embodiments, the wavelength may be from 950 nm to 1600 nm, and in other embodiments from 1000 nm to 1300 nm. The light source 304 may be one device with a plurality of integrated light sources comprising different modalities that may be operated by switching between the individual integrated light sources or may be a plurality of separate devices disposed at different areas of the intraoral camera system 302 and operated separately.

The intraoral camera system 302 may further comprise a processor and a colloidal quantum dot sensor 306. The processor may project light from the light source 304 as a projection beam 616 in a first direction towards at least one tooth 308. The processor may further record, by the colloidal quantum dot sensor 306, one or more surface light distri-bution images 126 produced at the surface of the at least one tooth 308 by the projected light; and compute, using the one or more surface light distribution images, a defect condition of the at least one tooth 308.

In an aspect herein, the intraoral camera system 302 may optionally further comprise a 3D sensor and/or a color sensor for 3D measurement and color measurement, respec-tively. FIG. 3 shows an illustrative embodiment depicting the colloidal quantum dot sensor 306 and a color sensor 316 wherein a beam splitter such as a first beam splitter 310 is used to split a monitoring beam 318 into a first light beam 320 that is recorded by the colloidal quantum dot sensor 306 as surface light distribution image 126 and a second light beam 322 that is directed by a second mirror 314 to be recorded by the color sensor 316 as color images. The color sensor 316 may be, for example an RGB color CMOS sensor.

The beam splitter may be an optical device that divides an incoming light beam into two or more separate beams by either transmitting or reflecting a portion of the incident light while allowing the rest to continue in an original direction. Dichroic beam splitters, for example, may split light based on its wavelength or color. Coatings may be selected in reflecting certain wavelengths while transmitting others.

Figure 4:
FIG. 4 depicts a sketch of an intraoral camera system in accordance with an illustrative embodiment.
Figure 4:
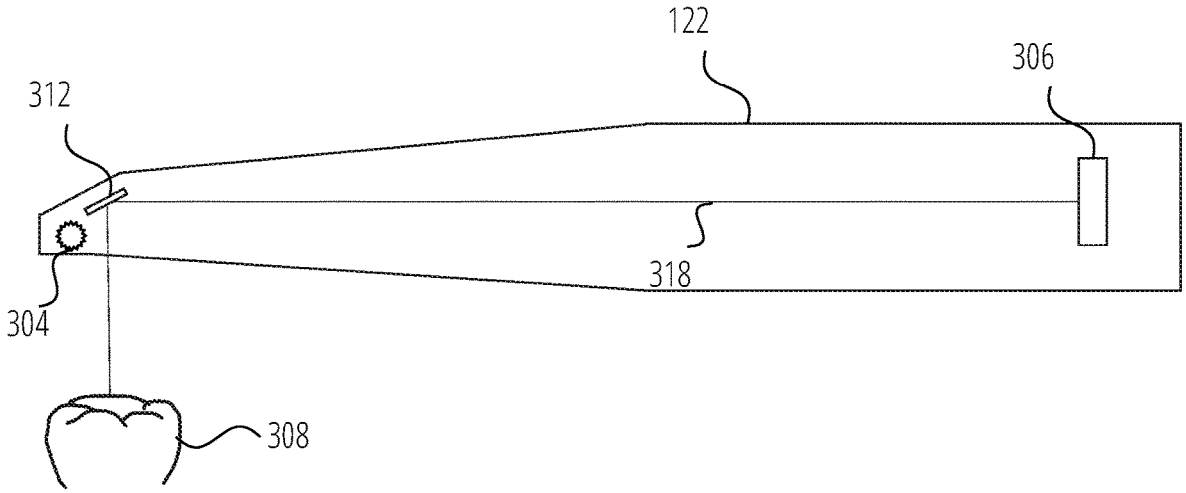

Alternatively, to a color sensor 316 being separate from a colloidal quantum dot sensor 306, the colloidal quantum dot sensor 306 may be configured with light sensitive elements that are sensitive to both infrared light and visible light to record both surface light distribution images and color images as shown in FIG. 4. For FIG. 4, the light source 304 may project both a full field white light illumination via a white light LED for color measurement (i.e., Color image and tooth shade detection) and structured or full field near-infrared (NIR) illumination via NIR LEDs of the light source for caries/tooth defect detection. The monitoring beam 318 may be directed to the imaging optics of the camera by the first mirror 312. Depending on the location of the light source 304, the optical path of the monitoring beam 318 may coincide, at least partially with the optical path of a projection beam.

Figure 5:
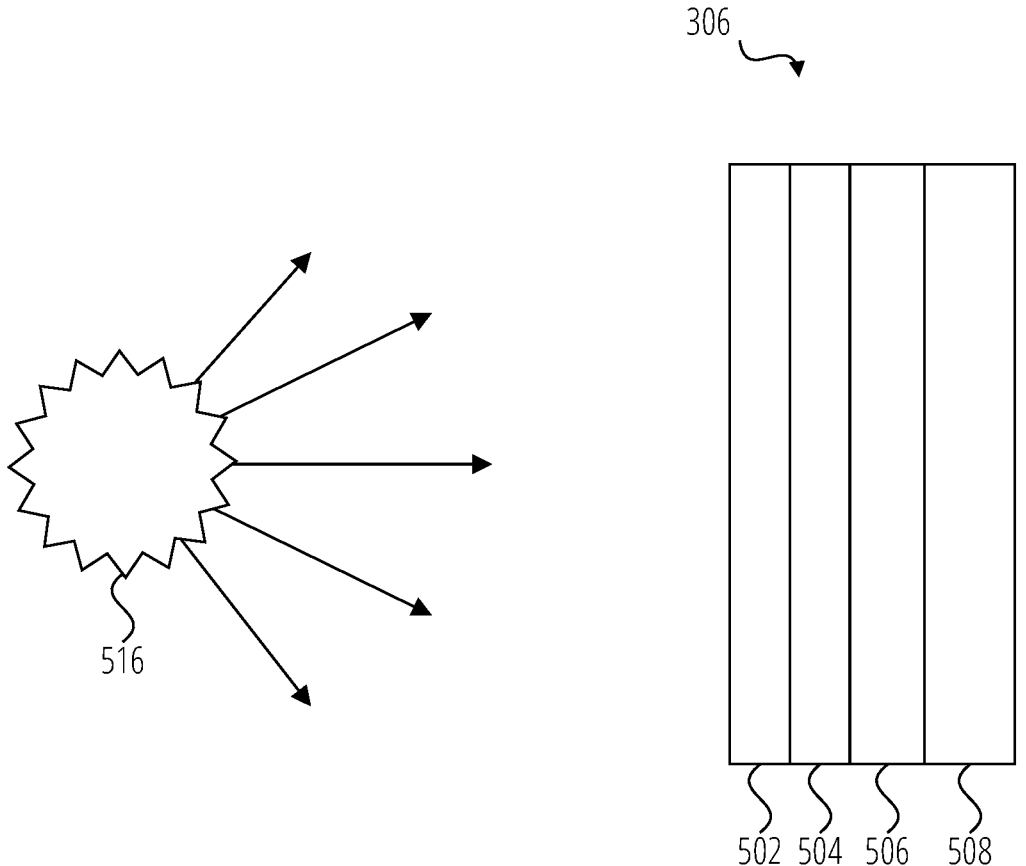
FIG. 5 depicts a sketch of a colloidal quantum dot sensor in accordance with an illustrative embodiment.

The colloidal quantum dot sensor 306 may be a type of sensor that uses colloidal quantum dots, i.e., nanoscale semiconductor particles that exhibit unique optical and electrical properties due to their small size and quantum confinement effects, as the sensing material. The colloidal quantum dots (CQDs) may be configured as photodetectors through a device structure that allows the CQDs to efficiently capture and convert incoming photons into electrical current. In an aspect herein, as depicted in FIG. 5, the colloidal quantum dot sensor 306 may comprise, for example, a substrate 502, which may be a solid material such as silicon, glass, or a flexible plastic substrate. Electrodes on the substrate may be utilized to collect photocurrent. For example, a transparent electrode 504 (e.g., indium tin oxide, ITO) may be placed on the surface where incident light 516 enters the sensor, and an opaque electrode 508 may be placed on an opposing side. The transparent electrode 504 may allow incident light to reach the CQD layer 506.

The CQD Layer 506 may comprise a thin layer of colloidal quantum dots covering the transparent electrode 504. The CQD layer 506 may comprise a predetermined thickness that enhances efficient absorption of photons while allowing easy charge carrier transport. Other layers such as an optional dielectric layer may be introduced between the CQD layer 506 and the substrate 502 to improve charge carrier separation and reduce the likelihood of charge recombination, whereas hole transport and electron transport layers may facilitate efficient movement of charge carriers. Even further, the electrodes may be coupled to external circuitry wherein photocurrent generated by the CQDs may be is collected by the electrodes and measured. An optional encapsulation (not shown) may be provided to encapsulate the sensor to protect the CQD layer 506 from ambient conditions.

By applying a bias voltage across the electrodes, an electric field may be generated within the CQD layer to separate photogenerated electrons and holes, driving them towards the respective electrodes. More specifically, when incident photons with energies greater than the bandgap of the CQD strike the CQD layer, they may be absorbed by the quantum dots, generating bound electron-hole pairs (excitons) which may be caused to separate by the electric field established by the bias voltage. Responsive to the electrons moving towards the electron-accepting electrode and holes moving towards the hole-accepting electrode, a photocurrent is generated and may be amplified via external circuitry and processed to generate the surface light distribution image 126. To generate the surface light distribution images, a mechanism may be used to spatially map the photocurrent across the CQD layer 506. For example, a pixelated electrode array approach may be utilized, wherein each pixel corresponds to a specific location on the CQD layer 506. The amplified photocurrent at each pixel is collected as data representing the light intensity at different locations across the CQD layer and effectively creating a two-dimensional array of values. The data may be subsequently further processed to reconstruct an image by arranging the pixel values in the correct spatial arrangement to form a visual representation of the tooth 308 that is illuminated by the projection beam. Of course, this example structure is not meant to be limiting as other structures may be obtained in view of the descriptions herein. For example, based on the specific design and requirements of the intraoral camera system 302, additional layers such as more dielectric layers and charge transport layers may be added to improve a performance of the CQD sensor. Additional electrodes may be connected to external circuitry for biasing and signal readout.

Even further, in addition to detecting infrared light such as near-infrared light, the colloidal quantum dot sensor 306 may optionally be constructed to further detect other modalities of light such as visible light within the visible spectrum, covering a range of wavelengths from approximately 400 nanometers (violet/blue) to 700 nanometers (red). This may be achieved by incorporating other quantum dots or photodiodes tuned to detect the desired new wavelengths. For example, by precisely controlling the size and composition of the quantum dots, the corresponding absorption and emission properties may be tailored to allowing for the design of dental imaging sensors comprising specific desired spectral sensitivities. In some cases, modified Bayer pattern filters including filter tiles for NIR additionally to RGB may be used. In some cases, as is shown in FIG. 4, the use of a beam splitter to split the monitoring beam 318 into a first light beam 320 and a second light beam 322 unlike what is depicted in FIG. 3, may be obviated. In general, the colloidal quantum dot sensor 306 may offer advantages such as tunable absorption spectra and high quantum efficiency for a plurality of dental imaging applications.

Figure 6:
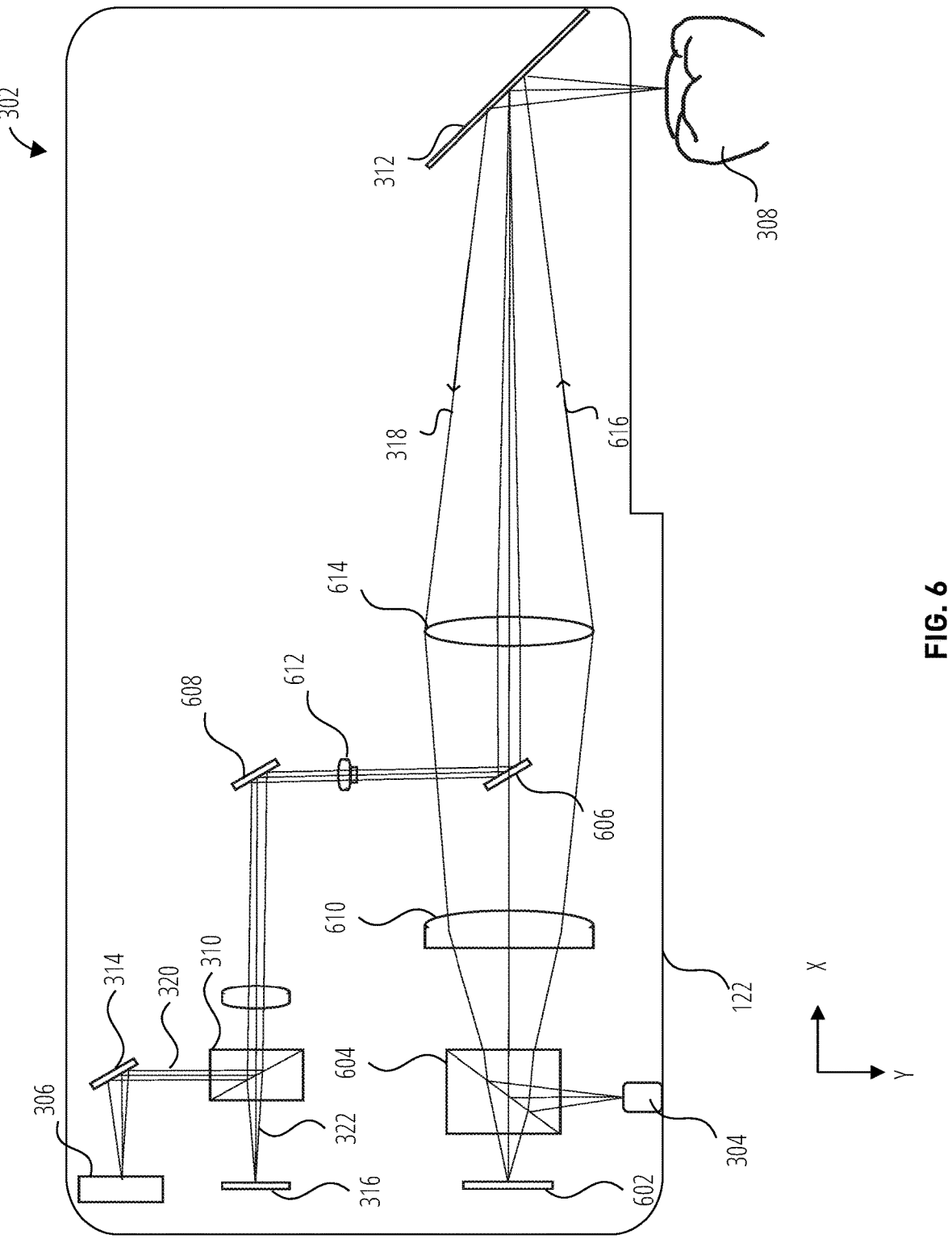
FIG. 6 depicts a sketch of an intraoral camera system in accordance with an illustrative embodiment.

FIG. 6 illustrates a sketch of an intraoral camera system 302 in accordance with another illustrative embodiment. The system depicts different optical paths generated for an intraoral camera comprising the colloidal quantum dot sensor 306, the color sensor 316 and the 3D sensor 602. Of course, this is not meant to be limiting as other intraoral camera comprising a colloidal quantum dot sensor 306 may be obtained in view of the descriptions.

The system comprises the intraoral camera 122, the light source 304, the colloidal quantum dot sensor 306, the color sensor 316, the 3D sensor 602, a first beam splitter 310, a second beam splitter 604, a first mirror 312, a second mirror 314, a third mirror 606, a fourth mirror 608, a first optics 610 such as a collimator, a polarizing filter 612, and an imaging optics 614. In the system of FIG. 6, light is projected from the light source 304 in a first direction towards the at least one tooth 308, the light source 304 is configured to generate at least infrared light in the wavelength range of 950 nm to 2500 nm or even longer. In an aspect, the light may be a temporal varying light or static pattern and the light source 304 may be, for example, an LED source with a microlens array or laser source. In an example, for color measurements (color image and tooth shade detection) via the color sensor 316, a full field white light illumination may be projected via a white light LED source. For near-infrared measurements via the colloidal quantum dot sensor 306, a structured or full field near-infrared light may be projected via a near-infrared LED source. The light may be projected as a projection beam 616 through a second beam splitter 604 onto an a first optics 610 such as a collimator and through a system aperture stop and imaging optics 614 onto the tooth 308. The light may subsequently be reflected by the tooth 308 as a monitoring beam 318 to be imaged onto the colloidal quantum dot sensor 306, the color sensor 316 and the 3D sensor 602. Image capture by the plurality of image sensors may be coordinated with the times in which different light modalities are projected by the light source. In the example configuration of FIG. 6, the second beam splitter 604 may separate outgoing projection beams of the light source 304 from incoming monitoring beams of the tooth 308. In an aspect, another modality of light such as blue light may be projected for 3D measurement.

For measurement by the sensors, the imaging optics 614 may be variable and may be configured with a depth of focus that may be much smaller than the thickness of the tooth 308 such that it may be used in, for example, confocal 3D measurement by the 3D sensor 602 as well as for measurement of infrared images by the colloidal quantum dot sensor 306 as the focal length is varied through the depth of the tooth 308. Specifically, the imaging optics 614 may be operated to mechanically or electrically adjust a focal length of the intraoral camera 122 to sweep over a depth (in the Y-axis as shown in FIG. 6) of the at least one tooth 308 and take a plurality of surface light distribution images 126 that may be combined to reconstruct an image covering the depth. In an aspect, the focal plane may be adjusted, for example mechanically, electronically, and/or automatically, by moving a lens of the imaging optics 614 forward and backward or changing the focal length of the imaging optics 614 electronically in a fixed position. In an aspect, a focal plane shift is achieved by changing the focal length of a variable lens via electronic lens deformation (using voltage variation). Further, the imaging optics 614 may be operated to adjust a depth of focus of the intraoral camera 122 to cover a depth of the at least one tooth 308 and take a sharp surface light distribution image covering the depth. These may also be applicable to images taken by the 3D sensor by varying the focal planes in the optical path of the 3D measurement accordingly. In an aspect, the focal plane of the color measurement optical path may be left unchanged by placing the variable imaging optics outside the optical path of the color measurement, such as configuring first optics 610 to be variable.

Further, by modulating the projection beam 616 with a predetermined frequency, signals corresponding to that frequency may be detected for further processing. Undesired reflections from the surface of the tooth 308 may produce unwanted effects in any captured images. Thus, the effects of such direct surface reflections may be reduced and/or eliminated using a polarization filter such as a polarizing filter 612 that filters out light with a same predetermined polarization as the polarization of the projection beam 616 by 90° cross polarization, for example. Light that has been scattered multiple times within the tooth has a somewhat random polarization and therefore can pass with less attenuation through the polarization filter 612 than light reflected directly at the surface of the tooth, which improves the image quality.

A fourth mirror 608 may direct a portion of the monitoring beam 318 to be imaged by the color sensor 316 and colloidal quantum dot sensor 306 wherein the first beam splitter 310 further splits the portion of the monitoring beam 318 into the first light beam 320 and the second light beam 322 for imaging.

The intraoral camera system 302 may further comprise a processing system such as the practice management system 128, the client 110, 112, 114, a processor, and/or a machine learning engine 124 configured to process and displaying data collected by the image sensors. For example, information obtained from one or images of one sensor may be used to further process images of another sensor. For example, 3D information from the 3D sensor 602 may be used to process or analyze near-infrared images/surface light distribution images of the colloidal quantum dot sensor 306. Further, color data of color sensor 316 and/or surface light distribution images may be mapped on a 3D model created from the 3D data of 3D sensor 602.

Turning now to FIG. 7, a routine 700 for capturing at least near-infrared images via the colloidal quantum dot sensor 306 is illustrated. The routine 700 may be performed with one or more processors or engines of the data processing environment 100.

In block 702, an intraoral camera 122 comprising a light source 304 may be provided. In block 704, light from the light source 304 may be projected in a first direction towards at tooth 308, the light source 304 being configured to generate at least infrared light in the wavelength range of 950 nm to 2500 nm. In block 706, the colloidal quantum dot sensor 306 records one or more surface light distribution images 126 produced at the surface of the at least one tooth by the projected light. In block 708, the one or more surface light distribution images are used to compute a defect condition of the at least one tooth 308.

In an aspect, the wavelength range may be 1000 nm to 1300 nm. In another aspect, the infrared light is projected as a structured light for generating spatial information about the optical properties of tooth material such as healthy and defective tooth material. More specifically, the vicinity of an illumination point may be observed using, for example, an illumination grid of beam points at the surface of the tooth 308. By illumination of an area on the tooth with an illumination grid pattern comprising spatially separated illumination spots and observing the non-illuminated vicinity between the illumination spots, the degradation of the intensity of the light around the spots may be obtained to generate additional information about the light scattering inside of the tooth, which is different for caries and other tooth defects as compared to healthy tooth material. In so doing, additional information otherwise unavailable with a full field illumination of the tooth, may be obtained. In an aspect, the illumination grid pattern may be projected at the same time or sequentially with other illumination used for 3D data generation or white light illumination.

In an aspect herein, the routine 700 may further comprise multimodal imaging comprising combinations of fluorescence imaging, visible imaging, NIR imaging, and/or the use of x-ray and MRI data in a diagnostic workflow. This may be facilitated with the practice management system 128 (PMS system). For example, the 3D data from the 3D sensor 602 may be available to optimize the 2D images. Herein, to improve 2D information from the colloidal quantum dot sensor 306 and/or color sensor 316 taking into consideration magnification factor changes as the intraoral camera 122 is moved further away from the tooth 308 the 3D data from the 3D sensor 602 which provides information about relative distances between points in a 3D coordinate system may be used. Tilt information between tooth surface and camera focal plane may also be used to correct for image distortion.

Further, data from the sensors and other diagnostic information such as patient-specific X-ray and MRI data from database 118 may be used to train a machine learning model and unseen data such as timeline data may be used by the trained machine learning model of the machine learning engine 124 to predict disease progression and enable better diagnostics. Even further, knowledge of the type of fillings and where and when fillings have been placed in a patient's oral cavity may be part of the input to the machine learning model, and thus input for training the model, to better diagnose tooth defects adjacent to fillings (e.g., secondary caries) or discriminate fillings from tooth defects. Processed and/or unprocessed NIR images provided by the colloidal quantum dot sensor 306 may enable to machine learning model to make more accurate predictions about disease progression.

In an aspect, a proposal of a progression of the defect condition may be generated using the one or more surface light distribution images 126 obtained via the colloidal quantum dot sensor 306 and a trained machine learning model that is trained using at least a plurality of training surface light distribution images from a training dataset. The training images may be obtained from a historical database that may in some cases be continuously updated with new images comprising different types of teeth e.g., molars, premolars incisors and different types of fillings and different filling positions on the tooth.

In another aspect, the defect condition may be computed using the one or more surface light distribution images 126 and a trained machine learning model that is trained using at least a plurality of training surface light distribution images. By providing the machine learning model with a large number of surface light distribution image that may be marked to show areas signifying tooth defects, the machine learning model may be trained to automatically detect tooth defects in unseen images.

In some aspects, the machine learning model may additionally be trained with other input data such as 3D data from the 3D sensor 602, and historical patient specific dental data such as the presence of fillings in the patient's oral cavity, MRI images and X-ray images. This may advantageously provide more accurate decisions about the presence or absence of tooth defects in a patient's oral cavity especially with the incorporation of higher wavelength infrared light capturing by the colloidal quantum dot sensor 306 that offers significantly improved images over conventional methods.

In another aspect, the defect condition may be computed based on computation of a change in light distribution in the one or more surface light distribution images caused by the defective tooth material. Spatial differences in surface light distribution images taken at points on the tooth 308 that are in close proximity to each other may aid in more accurate detections of tooth defects.

Thus, a computer implemented method, system or apparatus, and computer program product are provided in the illustrative embodiments for configuring intraoral cameras and other related features, functions, or operations. Where an embodiment or a portion thereof is described with respect to a type of device, the computer implemented method, system or apparatus, the computer program product, or a portion thereof, are adapted or configured for use with a suitable and comparable manifestation of that type of device.

Where an embodiment is described as implemented in an application, the delivery of the application in a Software as a Service (SaaS) model is contemplated within the scope of the illustrative embodiments. In a SaaS model, the capability of the application implementing an embodiment is provided to a user by executing the application in a cloud infrastructure. The user can access the application using a variety of client devices through a thin client interface such as a web browser, or other light-weight client-applications. The user does not manage or control the underlying cloud infrastructure including the network, servers, operating systems, or the storage of the cloud infrastructure. In some cases, the user may not even manage or control the capabilities of the SaaS application. In some other cases, the SaaS implementation of the application may permit a possible exception of limited user-specific application configuration settings.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, including but not limited to computer-readable storage devices as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Conclusion

Although techniques using, and apparatuses including, tooth defect detection have been described in language specific to features and/or methods, it is to be understood that the subject of the appended claims is not necessarily limited to the specific features or methods described. Rather, the specific features and methods are disclosed as example implementations of intraoral camera sensor configuration and use:

Example 1. A method comprising: providing an intraoral camera comprising a light source; projecting light from the light source in a first direction towards at least one tooth, the light source is configured to generate at least infrared light in the wavelength range of 950 nm to 2500 nm; recording, by a colloidal quantum dot (CQD) sensor, one or more surface light distribution images produced at the surface of the at least one tooth by the projected light; computing, using the one or more surface light distribution images, a defect condition of the at least one tooth.

Example 2. The method of example 1, wherein the wavelength range is 1000 nm to 1300 nm or 950 to 1600 nm.

Example 3. The method of example 1 or 2, wherein the light source is further configured to project visible light.

Example 4. The method of any previous example, wherein the infrared light is projected as a structured light for generating spatial information about the optical properties of healthy and defective tooth material.

Example 5. The method of example 4, wherein the structured light is projected as a grid of points.

Example 6. The method of any previous example, wherein the CQD sensor is further configured to record color images in addition to recording the one or more surface light distribution images.

Example 7. The method of any previous example, further comprising: recording by a color sensor, color images of the at least one tooth.

Example 8. The method of example 7, wherein a beam splitter is used to split a monitoring beam into a first light beam that is recorded by the CQD sensor and a second light beam that is recorded by the color sensor.

Example 9. The method of any previous example, wherein the intraoral camera is further configured to measure three-dimensional (3D) information about the at least one tooth.

Example 10. The method of any previous example, wherein the computing is performed by classifying the one or more surface light distribution images based on computation of a change in light distribution in the one or more surface light distribution images caused by the defective tooth material.

Example 11. The method of any previous example, further comprising: polarizing a projection beam of the light and a monitoring beam from the tooth and using corresponding polarization information to block tooth surface reflections.

Example 12. The method of any previous example, further comprising: operating a variable imaging optics to adjust a focal length of the intraoral camera to sweep over a depth of the at least one tooth and taking a plurality of surface light distribution images that are combined to reconstruct an overall image covering the depth.

Example 13. The method of any previous example, further comprising: operating a variable imaging optics to adjust a depth of focus of the intraoral camera to cover a depth of the at least one tooth and taking a sharp image covering the depth.

Example 14. The method of any previous example, further comprising: generating a proposal of a progression of the defect condition using the one or more surface light distribution images and a trained machine learning model that is trained using at least a plurality of training surface light distribution images.

Example 15. The method of examples 1-13, further comprising: computing the defect condition using the one or more surface light distribution images and a trained machine learning model that is trained using at least a plurality of training surface light distribution images.

Example 16. An intraoral camera system comprising: a light source configured to generate at least infrared light in the wavelength range of 950 nm to 2500 nm; a colloidal quantum dot (CQD) sensor; a processor, and a memory storing instructions that, when executed by the processor, configure the intraoral camera system to perform any of the examples 1-1.

Example 21. A non-transitory computer readable storage medium storing one or more programs that when executed by a processor cause the intra-oral camera system to perform any of the examples 1-15.

What is claimed is:

1. A method comprising:
providing an intraoral camera comprising a light source;
projecting light from the light source in a first direction towards at least one tooth, the light source is configured to generate at least infrared light in the wavelength range of 950 nm to 2500 nm, and visible light;
recording, by a colloidal quantum dot (CQD) sensor, one or more surface light distribution images produced at the surface of the at least one tooth by the projected light, wherein the COD sensor is further configured to record color images in addition to recording the one or more surface light distribution images; and
computing, using the one or more surface light distribution images, a defect condition of the at least one tooth.

2. The method of claim 1, wherein the wavelength range is 1000 nm to 1300 nm or 950 nm to 1600 nm.

3. The method of claim 1, wherein the infrared light is projected as a structured light for generating spatial information about optical properties of tooth material.

4. The method of claim 3, wherein the structured light is projected as a grid of points.

5. The method of claim 1, further comprising:
recording by a color sensor, color images of the at least one tooth.

6. The method of claim 5, wherein a beam splitter is used to split a monitoring beam into a first light beam that is recorded by the CQD sensor and a second light beam that is recorded by the color sensor.

7. The method of claim 1, wherein the intraoral camera is further configured to measure three-dimensional (3D) information about the at least one tooth.

8. The method of claim 1, wherein the computing is performed by classifying the one or more surface light distribution images based on computation of a change in light distribution in the one or more surface light distribution images caused by the defect condition.

9. The method of claim 1, further comprising:
polarizing a projection beam of the light and using predetermined polarization information to block tooth surface reflections.

10. The method of claim 1, further comprising:
operating a variable imaging optics to adjust a focal length of the intraoral camera to sweep over a depth of the at least one tooth and taking a plurality of surface light distribution images that are combined to reconstruct an overall image depth.

11. The method of claim 1, further comprising:
operating a variable imaging optics to adjust a depth of focus of the intraoral camera to cover a depth of the at least one tooth and taking sequential images covering the depth.

12. The method of claim 1, further comprising:
generating a proposal of a progression of the defect condition using the one or more surface light distribution images and a trained machine learning model that is trained using at least a plurality of training surface light distribution images.

13. The method of claim 1, further comprising:
computing the defect condition using the one or more surface light distribution images and a trained machine learning model that is trained using at least a plurality of training surface light distribution images.

14. An intraoral camera system comprising:
a light source configured to generate at least infrared light in the wavelength range of 950 nm to 2500 nm, and visible light;
a colloidal quantum dot (CQD) sensor; and
a processor configured to:
project light from the light source in a first direction towards at least one tooth;
record, by the COD sensor, one or more surface light distribution images produced at the surface of the at least one tooth by the projected light, wherein the COD sensor is further configured to record color images in addition to recording the one or more surface light distribution images; and
compute, using the one or more surface light distribution images, a defect condition of the at least one tooth.

15. The intraoral camera system of claim 14, further comprising:
a color sensor configured to record color images of the at least one tooth.

16. The intraoral camera system of claim 15, further comprising:
a beam splitter disposed in front of the color sensor, wherein the beam splitter splits a monitoring beam into a first light beam that is recorded by the CQD sensor and a second light beam that is recorded by the color sensor.

17. A non-transitory computer readable storage medium storing one or more programs that when executed by a processor cause an intraoral camera to:

project light from a light source of an intraoral camera in a first direction towards at least one tooth, the light source is configured to generate at least infrared light in the wavelength range of 950 nm to 2500 nm, and visible light;

record, by a colloidal quantum dot (CQD) sensor, one or more surface light distribution images produced at the surface of the at least one tooth by the projected light, wherein the CQD sensor is further configured to record color images in addition to recording the one or more surface light distribution images; and compute, using the one or more surface light distribution images, a defect condition of the at least one tooth.

\* \* \* \* \*